(12) United States Patent
Kampas et al.

(10) Patent No.: US 11,419,739 B2
(45) Date of Patent: *Aug. 23, 2022

(54) METHOD AND DEVICE FOR CONTROLLING AN ARTIFICIAL ORTHOTIC OR PROSTHETIC KNEE JOINT

(71) Applicant: OTTO BOCK HEALTHCARE PRODUCTS GMBH, Vienna (AT)

(72) Inventors: Philipp Kampas, Vienna (AT); Martin Seyr, Vienna (AT); Roland Pawlik, Vienna (AT); Constantin Pop, Ternitz (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 188 days.

This patent is subject to a terminal disclaimer.

(21) Appl. No.: 16/557,499

(22) Filed: Aug. 30, 2019

(65) Prior Publication Data
US 2019/0380847 A1 Dec. 19, 2019

Related U.S. Application Data

(63) Continuation of application No. 13/509,244, filed as application No. PCT/EP2010/006893 on Nov. 12, 2010, now Pat. No. 10,398,575.

(30) Foreign Application Priority Data

Nov. 13, 2009 (DE) .......................... 102009052895.4

(51) Int. Cl.
*A61F 2/60* (2006.01)
*A61F 2/64* (2006.01)
(Continued)

(52) U.S. Cl.
CPC .................. *A61F 2/64* (2013.01); *A61F 2/70* (2013.01); *A61F 2/68* (2013.01);
(Continued)

(58) Field of Classification Search
CPC ...... A61F 2/64; A61F 2/68; A61F 2/70; A61F 2002/5003; A61F 2002/5033; A61F 2002/701; A61F 2002/704
See application file for complete search history.

(56) References Cited

U.S. PATENT DOCUMENTS 6,755,870 B1 6/2004 Biedermann et al.
7,087,090 B2 8/2006 Andrysek et al.
(Continued)

FOREIGN PATENT DOCUMENTS

CN 1074109 11/1998
CN 101346110 A 1/2009
(Continued)

OTHER PUBLICATIONS

PCT International Search Report for International Patent Application No. PCT/EP2010/006893, dated Mar. 9, 2011.

*Primary Examiner* — Bruce E Snow
(74) *Attorney, Agent, or Firm* — Holland & Hart LLP

(57) ABSTRACT

A method for controlling an artificial orthotic or prosthetic joint of a lower extremity with a resistance unit to which at least one actuator is associated, via which the bending and/or stretching resistance is changed depending on sensor data. During the use of the joint, status information is provided via sensors. A device for carrying out such a method provides bending resistance that is increased or not lowered in the standing phase, when an inertial angle of a lower leg part is decreasing relative to a vertical direction and a front foot under pressure at the same time are identified.

18 Claims, 2 Drawing Sheets

(51) Int. Cl.
*A61F 2/70* (2006.01)
*A61F 2/50* (2006.01)
*A61F 2/68* (2006.01)
*A61F 2/76* (2006.01)
*G05D 1/02* (2020.01)
*B25J 9/16* (2006.01)

(52) U.S. Cl.
CPC .......... *A61F 2002/5003* (2013.01); *A61F 2002/5033* (2013.01); *A61F 2002/6818* (2013.01); *A61F 2002/701* (2013.01); *A61F 2002/704* (2013.01); *A61F 2002/7615* (2013.01); *A61F 2002/7625* (2013.01); *B25J 9/16* (2013.01); *G05D 1/02* (2013.01)

(56) References Cited

U.S. PATENT DOCUMENTS

| | | | |
|---|---|---|---|
| 7,455,696 B2 | 11/2008 | Bisbee, III et al. | |
| 7,731,759 B2* | 6/2010 | Pusch | A61F 2/70 623/44 |
| 8,231,688 B2 | 7/2012 | Fairbanks et al. | |
| 8,734,528 B2* | 5/2014 | Herr | B62D 57/032 623/24 |
| 2003/0125814 A1 | 7/2003 | Paasivaara | |
| 2006/0122710 A1 | 6/2006 | Bedard | |
| 2008/0114272 A1* | 5/2008 | Herr | A61F 2/70 600/595 |
| 2008/0288086 A1 | 11/2008 | Auberger et al. | |
| 2009/0171469 A1* | 7/2009 | Thorsteinsson | A61B 5/4585 623/26 |
| 2009/0265018 A1 | 10/2009 | Goldfarb et al. | |
| 2010/0023133 A1 | 1/2010 | Fairbanks et al. | |
| 2010/0305716 A1 | 12/2010 | Pusch et al. | |
| 2011/0087339 A1 | 4/2011 | Pusch et al. | |
| 2020/0397599 A1* | 12/2020 | Seifert | A61F 2/70 |

FOREIGN PATENT DOCUMENTS

| | | |
|---|---|---|
| DE | 19521464 C2 | 8/1999 |
| DE | 19859931 A1 | 7/2000 |
| DE | 102006021802 A1 | 11/2007 |
| DE | 102007053389 A1 | 5/2009 |
| DE | 102008008284 A1 | 8/2009 |
| EP | 1237513 B1 | 10/2004 |
| JP | 2005230207 A | 9/2005 |
| JP | 2009536050 | 10/2009 |
| JP | 2011502593 | 1/2011 |
| JP | 2011510766 | 4/2011 |
| RU | 2076670 C1 | 4/1997 |
| RU | 2089138 C1 | 9/1997 |
| RU | 2271779 C2 | 5/2005 |
| RU | 2254832 C1 | 6/2005 |
| RU | 2254834 C1 | 6/2005 |
| TW | 200930340 | 7/2009 |
| WO | 9218071 A1 | 10/1992 |

* cited by examiner

METHOD AND DEVICE FOR CONTROLLING AN ARTIFICIAL ORTHOTIC OR PROSTHETIC KNEE JOINT

CROSS REFERENCE TO RELATED APPLICATION

This application is a divisional of U.S. Pat. No. 10,398,575, filed 10 May 2012, and entitled METHOD AND DEVICE FOR CONTROLLING AN ARTIFICIAL ORTHOTIC OR PROSTHETIC KNEE JOINT, issued on 3 Sep. 2019, which is a U.S. national entry application from PCT International Patent Application No. PCT/EP2010/006893 filed 12 Nov. 2010, also entitled METHOD AND DEVICE FOR CONTROLLING AN ARTIFICIAL ORTHOTIC OR PROSTHETIC KNEE JOINT, which claimed benefit of German Patent Application No. 102009052895.4, filed 13 Nov. 2009, the disclosures of which are incorporated, in their entireties, by this reference.

STATEMENT REGARDING FEDERALLY SPONSORED RESEARCH OR DEVELOPMENT

This invention was made with government support under Contract No. W81XWH-06-1-0571 awarded by the United States Army Medical Research Acquisition Activity. The U.S. government has certain rights in the invention.

TECHNICAL FIELD

The disclosed subject matter relates to a method and a device for controlling an artificial orthotic or prosthetic joint of a lower extremity with a resistance device, which is assigned at least one actuator by way of which the bending and/or stretching resistance is changed in dependence on sensor data, information pertaining to the state being provided by way of sensors during the use of the joint. Apart from use in a prosthetic knee joint, the method and the device may also be meaningfully used, inter alia, for hip prostheses.

BACKGROUND

When extension assist springs are used for hip prostheses, there is the problem that the hip bends when loading is relieved, which in the case of a normal gait cycle is desired as a means of facilitating bending, but when walking backward brings the wearer into an undesired situation.

Artificial joints, in particular knee joints, for orthoses or prostheses have an upper connection part and a lower connection part, which are connected to each other by way of a joint device. In the case of a knee joint, receptacles for an upper leg stump or an upper leg rail are arranged on the upper connection part, while a lower leg shaft or a lower leg rail is arranged on the lower connection part. In the simplest case, the upper connection part and the lower connection part are connected to each other pivotably by a single-axis joint. Only in exceptional cases is such an arrangement sufficient for ensuring the desired success, for example support in the case of the use of an orthesis or a natural gait pattern in the case of use in a prosthesis.

In order to represent as naturally as possible or be conducive to the various requirements during the various phases of a step, or in the case of other tasks, resistance devices which offer a flexion resistance and/or an extension resistance are provided. The flexion resistance is used to set how easily the lower connection part can be pivoted with respect to the upper connection part in the direction of flexion. In the case of a knee joint, the flexion resistance is therefore used to set how easily the lower leg shaft or the lower leg rail swings backward in relation to the upper leg shaft or the upper leg rail when a force is applied. The extension resistance retards the forward movement of the lower leg shaft or the lower leg rail and can form a stretching stop. In the case of other types of joint, such as the hip joint or the ankle joint, these statements apply in a way corresponding to the kinematic conditions.

It is possible by using settable resistance devices to adapt the respective flexion resistance and/or extension resistance to the user of the prosthetic or orthotic device or to make allowance for different gait or movement situations, in order to be able to offer an adapted resistance under changing conditions.

DE 10 2008 008 284 A1 discloses an orthopedic knee joint with an upper part and a lower part arranged pivotably thereon and assigned a number of sensors, for example a bending angle sensor, an acceleration sensor, an inclination sensor and/or a force sensor. The extension stop is determined in dependence on the sensor data determined.

DE 10 2006 021 802 A1 describes a control of a passive prosthetic knee joint with adjustable damping in the direction of flexion for the adaptation of a prosthetic device with upper connecting means and a connecting element to an artificial foot. The adaptation is for climbing stairs, a low-torque lift of the prosthetic foot being detected and the flexion damping being lowered in a lifting phase to below a level that is suitable for walking on level ground. The flexion damping may be raised in dependence on the changing of the knee angle and in dependence on the axial force acting on the lower leg.

DE 10 2007 053 389 A1 describes a method and a device for controlling an orthopedic joint of a lower extremity with at least one degree of freedom, with an adjustable actuator for adapting to walking situations that differ from walking on level ground an orthopedic device which has upper connecting means to a limb and an orthopedic joint arranged in a jointed manner distally in relation to the connecting means. In this case, a number of parameters of the orthopedic device are detected by way of sensors, the detected parameters are compared with criteria that have been produced on the basis of a number of parameters and/or parameter profiles and stored in a computer unit, and a criterion that is suitable on the basis of the parameters or parameter profiles determined is selected. On the basis of the criterion selected, bending resistances, bending extents, driving forces and/or how they vary over time are set in order to control special functions that deviate from walking on level ground. A tilting angle of part of the orthopedic device in space and/or a variation of a change in tilting angle of part of the orthopedic device may be used as parameters.

EP 1237513 B1 describes a prosthesis or orthesis with a control device and a sensor coupled therewith, which detects an angle of inclination with respect to a fixed line of a part connected to a joint. On the basis of the angle of inclination data, the movement properties of the joint change, that is to say the joint is braked or released.

Furthermore, the prior art discloses what are known as brake knee joints, in which the flexion resistance and extension resistance are mechanically increased as axial loading becomes greater. This is achieved in the simplest case by providing two braking surfaces which are pressed onto each other by a ground reaction force. Such a configuration cannot be used on the braking device for modern prosthetic knee joints with controlled resistance devices.

SUMMARY

One object of the disclosed subject matter is to provide a method and a device with which it is possible automatically to load the knee with an increased resistance or to lock it when walking backward, without a deliberate activation or deactivation of the mode having to be performed.

The method for controlling an artificial orthotic or prosthetic knee joint with a resistance device, which is assigned at least one actuator by way of which the bending (e.g., flexion) and/or stretching (e.g., extension) resistance is changed in dependence on sensor data, information pertaining to the state being provided by way of sensors during the use of the joint, provides that the bending resistance is increased, or not reduced, in the standing phase if an inertial angle of a lower leg part that is decreasing in the direction of the vertical and a simultaneously loaded forefoot are determined. The coupling of the sensor variable of a decreasing inertial angle of a lower leg part in the direction of the vertical with the presence of a loading of the forefoot makes it possible for walking backward to be reliably detected and no swing phase to be triggered, that is to say not to reduce the flexion resistance in order to avoid an unwanted bending of the knee joint if, when walking backward, the fitted leg is placed backward and set down. This makes it possible for the fitted leg to be loaded in the bending direction without buckling, so that it is possible for a patient fitted with a prosthesis or orthosis to walk backward without having to activate a special locking mechanism. Should walking backward be detected, it is advantageous if the bending resistance is increased, or not reduced, so that a triggering of the swing phase is in any event precluded.

A development of the disclosed subject matter provides that the resistance is increased, or at least not reduced, if the inertial angle velocity of a joint part falls below a threshold value or, to put it another way, a swing phase with a lowering of the flexion resistance is initiated when the inertial angle velocity exceeds a predetermined threshold value. It is likewise possible that it is determined by way of the determination of the inertial angle of a joint part, in particular of the lower leg part, and the inertial angle velocity of a joint part, in particular of the lower leg part, that the user of the prosthesis or user of the orthesis is moving backward and needs a knee joint that is locked or greatly retarded against flexion. Accordingly, the resistance is increased if it is not yet sufficiently great, so that the knee joint can possibly be locked.

Furthermore, it may be provided that the variation in the loading of the forefoot is determined and the resistance is increased, or not reduced, if, with a decreasing inertial angle of the lower leg part, the loading of the forefoot is reduced. While, in the case of a forward movement, after the heel strike the loading of the forefoot only increases when the lower leg part has been pivoted forward beyond the vertical, when walking backward the loading of the forefoot decreases when there is a decreasing inertial angle, so that in the presence of both states, that is a decreasing inertial angle and a decreasing loading of the forefoot, walking backward can be concluded. Accordingly, the resistance is then increased to that value that is provided for walking backward.

It may also be provided that the resistance is increased, or not reduced, if the knee angle is less than 15°. This rules out the possibility that the knee joint can be locked and no longer bent during the swing phase and when there is a bended knee, with corresponding angles or angle velocities. Walking backward can consequently only take place when the fitted leg is in a stretched or almost stretched position. It may likewise be provided that the resistance is increased, or not reduced, even though the knee angle is more than 15° if the angle velocity is very small or there is a static state, that is to say the fitted leg has been set back and no walking movement is initiated. In this static case, it is difficult to detect whether a forward or backward movement will take place.

A further characteristic may be the knee torque, which is detected and serves as a basis for whether the resistance is increased, or not reduced. If a knee torque acting in the direction of flexion is determined, that is to say if the prosthetic foot has been set down and a flexion torque in the knee is detected, there is a situation in which walking backward must be assumed, so that then a flexion lock, that is to say an increase of the resistance to a value that does not make bending readily possible, is justified.

The inertial angle of the lower leg part may be determined directly by way of a sensor device which is arranged on the lower leg part or from the inertial angle of another connection part, for example the upper leg part, and a likewise determined joint angle. Since the joint angle between the upper leg part and the lower leg part may also be used for other control signals, the multiple arrangement of sensors and the multiple use of the signals provide a redundancy, so that, even in the event of failure of one sensor, the functionality of the prosthesis or orthesis continues to be preserved. A changing of the inertial angle of a joint part can be determined directly by way of a gyroscope or from the differentiation of an inertial angle signal of the joint part or from the inertial angle signal of a connection part and a joint angle.

The flexion resistance may be reduced in the standing phase to a value suitable for the swing phase if an inertial angle of the lower leg part that is increasing in relation to the vertical is determined. The increasing inertial angle of the lower leg part indicates that the user of the prosthesis or user of the orthesis is in a forward movement, the distal end of the lower leg part being assumed as the hinge point. It is provided that the reduction only takes place whenever the increase in the inertial angle is above a threshold value. Furthermore, the resistance may be reduced if the movement of the lower leg part in relation to the upper leg part is not bending, that is to say is stretching or remains constant, which suggests a forward movement. Equally, the resistance may be reduced if there is a stretching knee torque.

Furthermore, it may be provided that the distance of the ground reaction force vector from a joint part is determined and the resistance is reduced whenever a threshold value of the distance is exceeded, that is to say whenever the distance of the ground reaction force vector lies above a minimum distance from a joint part, for example from the longitudinal axis of the lower leg part at a specific height or from the pivot axis of the knee joint.

The resistance may again be reduced to a value that is suitable for the swing phase if it has been determined that the knee torque has changed from stretching to bending. The reduction in this case takes place directly after the changing of the knee torque from stretching to bending.

Furthermore, it may be provided that, after a reduction, the resistance is increased again to the value in the standing phase if, within a fixed time after the reduction of the resistance, a threshold value for an inertial angle of a joint component, for an inertial angle velocity, for a ground reaction force, for a joint torque, for a joint angle or for a distance of a force vector from a joint component is not reached. To put it another way, the joint is set again to the standing phase state unless, within a fixed time after a change to the swing phase state, a swing phase is actually established. The basis for this is that the triggering of the swing phase has already taken place before the tip of the foot has left the ground, in order to make a prompt initiation of the swing phase possible. Should, however, the swing phase then not be initiated, as is the case for example when there is a circumduction movement, it is necessary to switch again to the safe standing phase resistance. Provided for this purpose is a timer, which checks whether within a specific time an expected value for one of the variables referred to above is present. The resistance remains reduced, that is to say the swing phase remains activated, if a joint angle increase is detected, that is to say if a swing phase is actually initiated. It is likewise possible that, after the threshold value is reached and clearance for the swing phase is given, the timer is only switched on when a second threshold value that is smaller than the first threshold value is fallen below. It may therefore be provided that, after a reduction, the resistance is increased again to the value for the standing phase if, after the reduction of the resistance and reaching a threshold value for an inertial angle of a joint component, an inertial angle velocity, a ground reaction force, a joint torque, a joint angle or a distance of a force vector from a joint component after the reduction, a further threshold value for an inertial angle, for an inertial angle velocity, for a ground reaction force, for a joint torque, for a joint angle or for a distance of a force vector from a joint component is not reached within a fixed time.

In order to control artificial joints on the basis of sensor data, those sensors that are specifically necessary to ensure a safety standard in the detection of gait phase transitions are arranged. If sensors that go beyond the minimum required are used, for example to raise the safety standard, this redundancy of sensors makes it possible to realize controls that do not use all of the sensors arranged in or on the joint and nevertheless maintain a minimum standard of safety. It is provided that the redundancy of the sensors is used to realize alternative controls which, in the case of a failure of sensors, still make walking with a swing phase possible with the sensors that are still operating, and offer a minimum standard of safety.

A device for carrying out the method described above, with a settable resistance device, which is arranged between two components of an artificial orthotic or prosthetic joint that are mounted one against the other in a jointed manner, with a control device and sensors that detect information pertaining to the state of the device, provides that a setting device is provided and that a loading-dependent change in resistance can be activated and/or can be deactivated by way of the setting device. In dependence on the presence or absence of the loading of the forefoot, the resistance device is activated or deactivated. Along with an automatic detection of walking backward and the automatic adaptation of the resistance, this allows a deliberate activation of the walking backward mode to be achieved, and it is likewise possible to switch off this mode and remove it from the standard program of the knee control.

BRIEF DESCRIPTION OF THE DRAWINGS

An example of the disclosed subject matter is explained in more detail below with reference to the figures. In the drawing.

DETAILED DESCRIPTION

Figure 1:
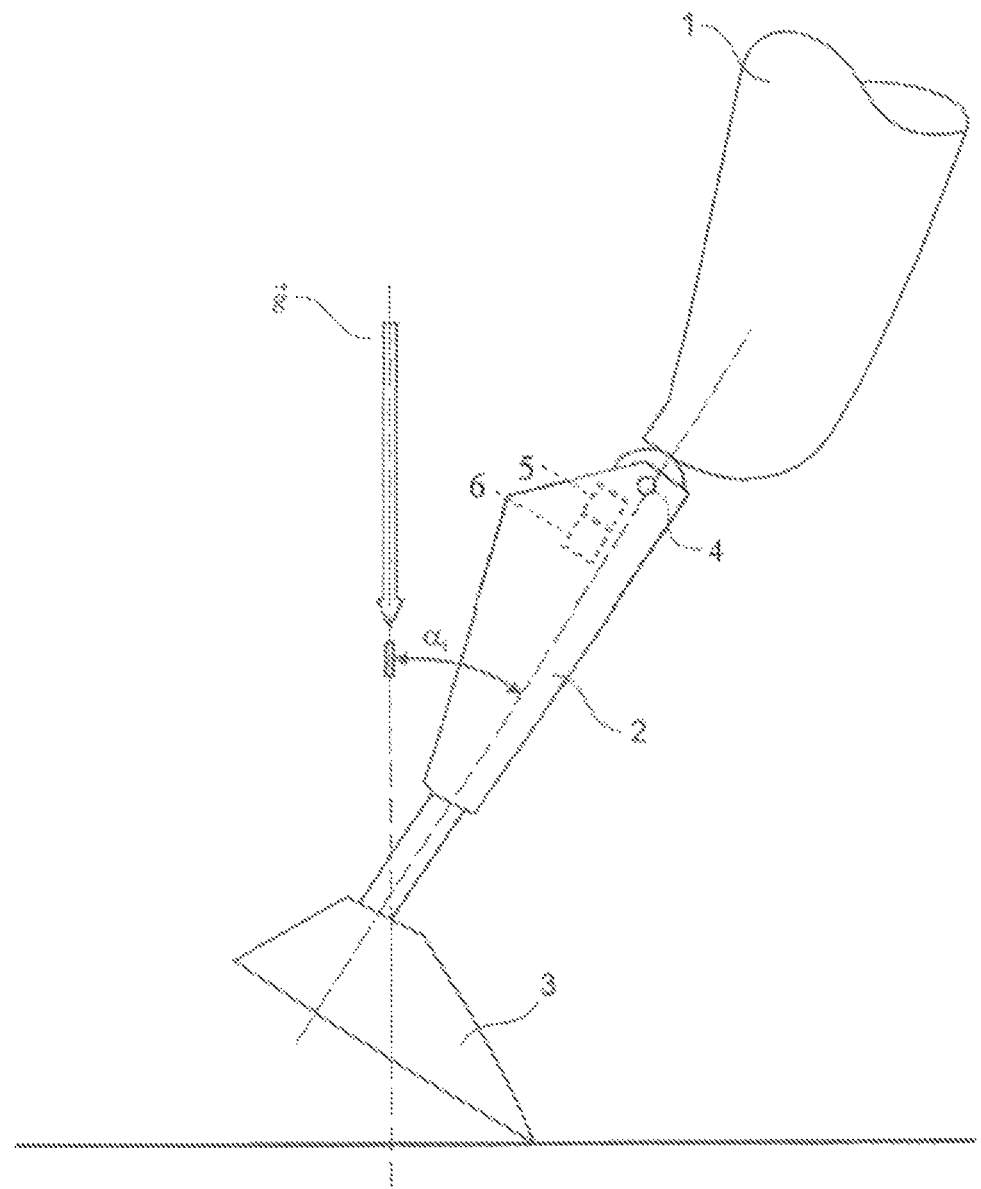
FIG. 1 shows a schematic representation of a prosthesis when walking backward.

In FIG. 1, a prosthesis with an upper leg part 1 and a lower leg part 2 mounted thereon in a jointed manner is shown. Arranged at the distal end of the lower leg part 2 is a prosthetic foot 3. The lower leg part 2 is connected to the upper leg part 1 in a jointed manner by way of a prosthetic knee joint 4. A resistance device 5, which is operated via an actuator 6, controls resistance to flexion and extension movement of the knee joint. The upper leg part 1 is designed in the form of an upper leg shaft, so that an upper leg stump can be inserted and secured therein. The inertial angle $\alpha_1$ is the absolute angle of the joint component in relation to the vertical, from which the inertial angle velocity $\bar{\omega}_1$ is obtained as the derivative of the inertial angle with respect to time. Starting from a standing situation, when walking backward the fitted leg, in the present case the prosthesis, is set backward, that is to say opposite to the normal viewing direction of a user of the prosthesis. This has the effect that the inertial angle $\alpha_1$ of the lower leg part 2 initially increases in relation to the direction of gravitational force, which is indicated by the gravitational force vector g, until the prosthetic foot 3 is set down on the ground. After setting down, the pivot point is the prosthetic foot. When the patient walks backward, after setting down the inertial angle $\alpha_1$ will decrease, and so the inertial angle velocity $\bar{\omega}_1$ will be negative. Consequently, in this situation it is possible to distinguish between walking forward and walking backward by way of the inertial angle velocity $\bar{\omega}_1$. Whereas when walking forward in a corresponding situation, that is to say with loading of the forefoot and the prosthesis tilted forward and a positive inertial angle velocity $\bar{\omega}_1$, the resistance should be reduced for the swing phase, when walking backward, in this situation, that is to say with loading of the forefoot and the prosthesis tilted forward and a negative inertial angle velocity $\bar{\omega}_1$, the resistance should not be reduced for a swing phase. The inertial angle $\alpha_1$ is obtained, for example as depicted, from the vertical in relation to the longitudinal extent of the lower leg part 2. The distal end of the lower leg part 2 should be assumed here as the pivot point or hinge point for determining the increasing inertial angle $\alpha_1$, so that the inertial angle $\alpha_1$ is obtained, as depicted, from the vertical in relation to the longitudinal extent of the lower leg part 2. The longitudinal extent or longitudinal axis of the lower leg part 2 runs through the pivot axis of the prosthetic knee joint 4 and preferably likewise through a pivot axis of the ankle joint or else centrally through a connection point between the prosthetic foot 3 and the lower leg part 2. The inertial angle $\alpha_1$ of the lower leg part 2 can be determined directly by a sensor device arranged on the lower leg part 2; as an alternative to this, it may be determined by way of a sensor on the upper leg part 1 and a knee angle sensor, which detects the angle between the upper leg part 1 and the lower leg part 2.

For determining the inertial angle velocity, the changing of the inertial angle $\alpha_1$ over time is determined, so that an angle velocity $\bar{\omega}_1$ is obtained, and this can be determined in terms of the amount and the direction. If there is then a specific inertial angle $\alpha_1$ and a specific inertial angle velocity $\bar{\omega}_1$, a swing phase is initiated if a specific threshold value for the inertial angle velocity $\bar{\omega}_1$ is exceeded. If there is a decreasing inertial angle $\alpha_1$, and additionally also a loading of the forefoot, walking backward can be concluded, so that the flexion resistance is not reduced but is retained or increased, in order not to initiate a swing phase flexion.

Figure 2:
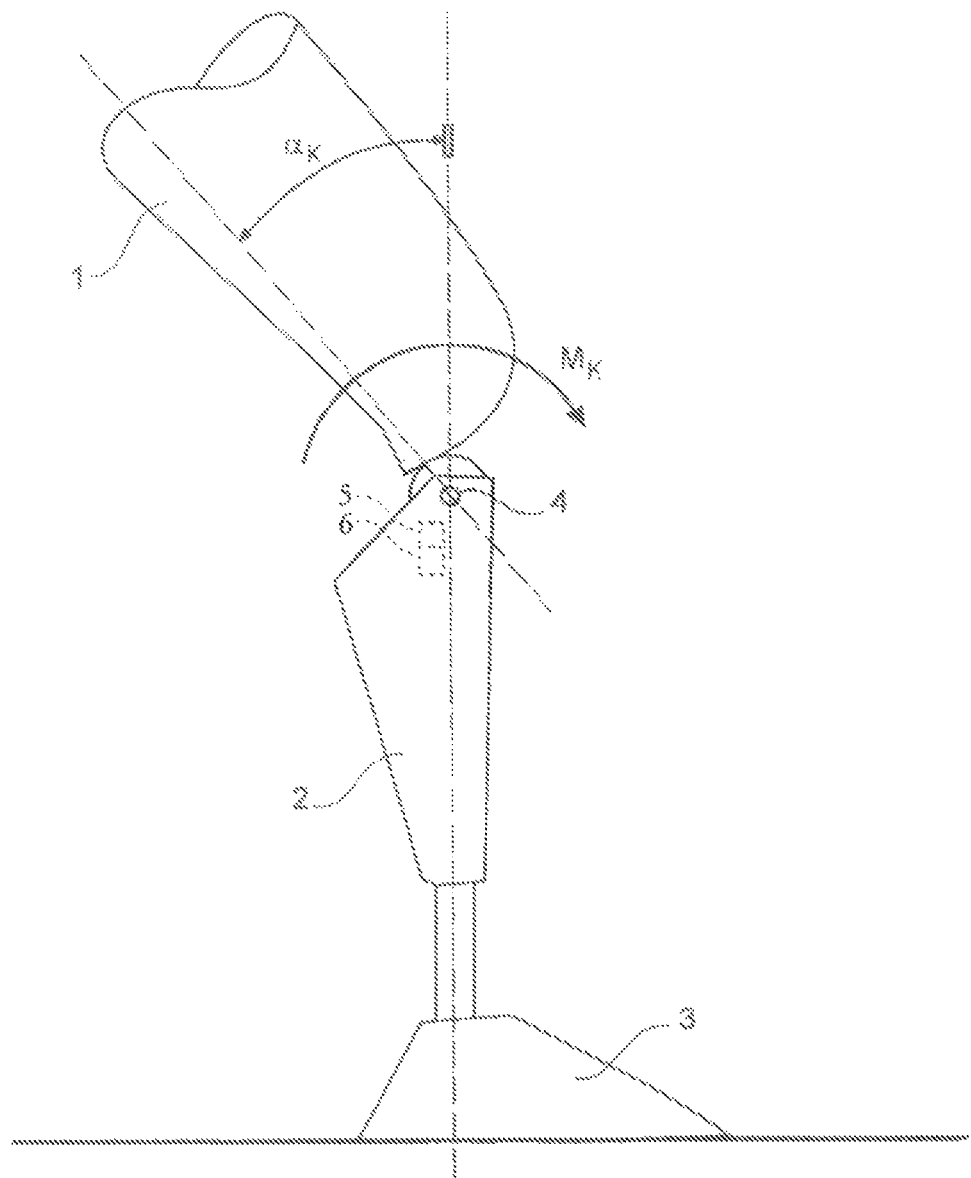
FIG. 2 shows a schematic representation of a prosthesis in the bent position.

In FIG. 2, the prosthesis is shown in a state in which it has been set down flat on the ground and serves for the sign convention in this description. With other sign conventions, there may correspondingly be other designations. The knee angle $\alpha_K$ corresponds in this case to the angle of the upper leg part 1 with respect to the lower leg part 2, the knee angle velocity $\bar{\omega}_K$ is correspondingly obtained from the derivative of the knee angle $\alpha_K$ with respect to time. A knee torque $M_K$ is effective about the joint axis of the prosthetic knee joint 4, assumed to be acting positively in the stretching direction. If a joint angle velocity is present, it is assumed that the joint is being bent under loading. Consequently, a reduction of the resistance would cause an abruptly unsafe situation and must therefore be precluded. The same applies in the case of too great a knee angle $\alpha_K$, which indicates that the prosthesis is already bent and, once again, a reduction of the resistance would cause an abruptly unsafe situation and must therefore be precluded.

In addition, other inertial angles that must reach a fixed threshold value in order for a decision on walking backward or the initiation of a swing phase to be taken may also be defined. The inertial angles of the lower leg part 2, the prosthetic foot 3 or the upper leg part 1 may be used for this.

ILLUSTRATIVE EMBODIMENTS

P1. A method for controlling an artificial orthotic or prosthetic joint of a lower extremity with a resistance device, which is assigned at least one actuator by way of which the bending and/or stretching resistance is changed in dependence on sensor data, information pertaining to the state being provided by way of sensors during the use of the joint, characterized in that the bending resistance is increased, or not reduced, in the standing phase if an inertial angle of a lower leg part that is decreasing in the direction of the vertical and a simultaneously loaded forefoot are determined.

P2. The method as described in paragraph P1, characterized in that the resistance is increased, or not reduced, if the inertial angle velocity of a joint part falls below a threshold value.

P3. The method as described in paragraph P1 or P2, characterized in that the variation in the loading of the forefoot is determined and the resistance is increased, or not reduced, if, with a decreasing inertial angle of the lower leg part, the loading of the forefoot is decreased.

P4. The method as described in one of the preceding paragraphs, characterized in that the resistance is increased, or not reduced, if the knee angle is less than 15°.

P5. The method as described in one of the preceding paragraphs, characterized in that a knee torque is detected and the resistance is increased, or not reduced, if a knee torque acting in the direction of flexion is determined.

P6. The method as described in one of the preceding paragraphs, characterized in that the inertial angle of the lower leg part is determined either directly or from the inertial angle of another connection part and a joint angle.

P7. The method as described in one of the preceding paragraphs, characterized in that a changing of the inertial angle of a joint part is determined directly by way of a gyroscope or from the differentiation of an inertial angle signal of the joint part or from the inertial angle signal of a connection part and a joint angle.

P8. The method as described in one of the preceding paragraphs, characterized in that the resistance is reduced in the standing phase if an inertial angle of the lower leg part that is increasing in relation to the vertical is determined.

P9. The method as described in one of the preceding paragraphs, characterized in that the resistance is reduced if the movement of the lower leg part in relation to the upper leg part is not bending.

P10. The method as described in one of the preceding paragraphs, characterized in that the resistance is reduced if there is a stretching knee torque.

P11. The method as described in one of the preceding paragraphs, characterized in that the distance of the ground reaction force vector from a joint part is determined and the resistance is reduced if a threshold value of the distance is exceeded.

P12. The method as described in one of the preceding paragraphs, characterized in that, after a reduction, the resistance is increased again to the value for the standing phase if, within a fixed time after the reduction of the resistance, a threshold value for an inertial angle of a joint component, for an inertial angle velocity, for a ground reaction force, for a joint torque, for a joint angle or for a distance of a force vector from a joint component is not reached.

P13. The method as described in one of the preceding paragraphs, characterized in that, after a reduction, the resistance is increased again to the value for the standing phase if, after the reduction of the resistance and reaching a threshold value for an inertial angle of a joint component, an inertial angle velocity, a ground reaction force, a joint torque, a joint angle or a distance of a force vector from a joint component after the reduction, a further threshold value for an inertial angle, for an inertial angle velocity, for a ground reaction force, for a joint torque, for a joint angle or for a distance of a force vector from a joint component is not reached within a fixed time.

P14. The method as described in paragraph P12 or P13, characterized in that the resistance remains reduced if a joint angle increase is detected.

P15. The method as described in one of the preceding paragraphs, characterized in that, in the case of a failure of devices for detecting torques, forces and/or joint angles, alternative control algorithms on the basis of the remaining devices are used for changing the stretching and/or bending resistance.

P16. A device for carrying out the method as described in one of the preceding paragraphs, with a settable resistance device, which is arranged between two components of an artificial orthotic or prosthetic knee joint that are mounted one against the other in a jointed manner, with a control device and sensors that detect information pertaining to the state of the device, characterized in that a setting device is provided and in that a loading-dependent change in resistance can be activated and/or can be deactivated by way of the setting device.

The invention claimed is:

1. A method for controlling an artificial orthotic or prosthetic device, the artificial orthotic or prosthetic device comprising:
    an upper leg part and a lower leg part coupled together at a knee joint;
    a foot coupled to the lower leg part;
    a plurality of sensors; and
    at least one actuator configured to adjust the flexion resistance of the knee joint;
    the method comprising:
    determining, using information from at least one of the plurality of sensors, that an inertial angle of the lower leg part is decreasing relative to a vertical direction and an inertial angle velocity of the lower leg part is below a threshold value, wherein the inertial angle includes an angle between the lower leg part and a vertical line positioned behind the lower leg part and extending through an ankle portion of the prosthetic device; and maintaining or increasing the flexion resistance of the knee joint in a standing phase based upon the inertial angle of the lower leg part decreasing relative to the vertical direction at the same time as the inertial angle velocity of the lower leg part is below the threshold value.

2. The method of claim 1, wherein the foot comprises a forefoot, the method further comprising:

determining, using information from at least one of the plurality of sensors, that the forefoot is loaded; and wherein the step of maintaining or increasing the flexion resistance of the knee joint in the standing phase includes maintaining or increasing the flexion resistance of the knee joint in the standing phase based upon the forefoot being loaded.

3. The method of claim 2, further comprising:

determining, using information from at least one of the plurality of sensors, that the loading on the forefoot is decreasing;

wherein the step of maintaining or increasing the flexion resistance of the knee joint in the standing phase comprises maintaining or increasing the flexion resistance of the knee joint in the standing phase based upon the decreasing loading on the forefoot.

4. The method of claim 1, further comprising:

determining, using information from at least one of the plurality of sensors, that the angle of the knee joint is less than 15°;

wherein the step of maintaining or increasing the flexion resistance of the knee joint in the standing phase comprises maintaining or increasing the flexion resistance of the knee joint in the standing phase based upon the angle of the knee joint being less than 15°.

5. The method of claim 1, further comprising:

determining, using information from at least one of the plurality of sensors, that torque on the knee joint is in the flexion direction;

wherein the step of maintaining or increasing the flexion resistance of the knee joint in the standing phase comprises maintaining or increasing the flexion resistance of the knee joint in the standing phase based upon the torque on the knee joint being in the flexion direction.

6. The method of claim 1, further comprising:

determining the inertial angle of the lower leg part directly from a sensor positioned on the lower leg part; or determining the inertial angle of the lower leg part from the inertial angle of another joint component of the artificial orthotic or prosthetic device and the angle of the knee joint.

7. The method of claim 1, further comprising:

determining that the inertial angle of the lower leg part is decreasing relative to the vertical direction directly by way of a gyroscope positioned on the lower leg part; or determining that the inertial angle of the lower leg part is decreasing relative to the vertical direction by differentiation of a signal from a sensor configured to determine the angle of the knee joint; or determining that the inertial angle of the lower leg part is decreasing relative to the vertical direction from a signal of a sensor configured to determine the inertial angle of another joint component of the artificial orthotic or prosthetic device and the angle of the knee joint.

8. The method of claim 1, further comprising:

determining, using information from at least one of the plurality of sensors, that the inertial angle of the lower leg part is increasing relative to the vertical direction; and reducing the flexion resistance of the knee joint based upon the inertial angle of the lower leg part increasing relative to the vertical direction.

9. The method of claim 1, further comprising:

determining, using information from at least one of the plurality of sensors, that movement of the lower leg part relative to the upper leg part is not in the flexion direction; and reducing the flexion resistance of the knee joint based upon movement of the lower leg part relative to the upper leg part not being in the flexion direction.

10. The method of claim 1, further comprising:

determining, using information from at least one of the plurality of sensors, that torque on the knee joint is in the extension direction; and reducing the flexion resistance of the knee joint based upon the torque on the knee joint being in the extension direction.

11. The method of claim 1, further comprising:

reducing the flexion resistance of the knee joint;

determining, using information from at least one of the plurality of sensors, that at least one of an inertial angle of a joint component of the artificial orthotic or prosthetic device, an inertial angle velocity of a joint component of the artificial orthotic or prosthetic device, a ground reaction force, torque on the knee joint, the angle of the knee joint, or a distance of a force vector from a joint component of the artificial orthotic or prosthetic device did not reach a threshold value within a fixed time after reducing the flexion resistance of the knee joint; and increasing the flexion resistance of the knee joint based upon at least one of the inertial angle of a joint component of the artificial orthotic or prosthetic device, the inertial angle velocity of a joint component of the artificial orthotic or prosthetic device, the ground reaction force, torque on the knee joint, the angle of the knee joint, or the distance of the force vector from a joint component of the artificial orthotic or prosthetic device not reaching the threshold value within the fixed time after reducing the flexion resistance of the knee joint.

12. The method of claim 11, further comprising:

determining, using information from at least one of the plurality of sensors, that the angle of the knee joint is increasing; and maintaining the reduced flexion resistance of the knee joint based upon the angle of the knee joint increasing.

13. The method of claim 1, further comprising:

reducing the flexion resistance of the knee joint;

determining, using information from at least one of the plurality of sensors, that at least one of an inertial angle of a joint component of the artificial orthotic or prosthetic device, an inertial angle velocity of a joint component of the artificial orthotic or prosthetic device, a ground reaction force, torque on the knee joint, the angle of the knee joint, or a distance of a force vector from a joint component of the artificial orthotic or prosthetic device did reach a first threshold value within a first fixed time after reducing the flexion resistance of the knee joint; and maintaining the reduced flexion resistance of the knee joint based upon at least one of the inertial angle of a joint component of the artificial orthotic or prosthetic device, the inertial angle velocity of a joint component of the artificial orthotic or prosthetic device, the ground reaction force, torque on the knee joint, the angle of the knee joint, or the distance of the force vector from a joint component of the artificial orthotic or prosthetic device reaching the first threshold value within the first fixed time after reducing the flexion resistance of the knee joint;

determining, using information from at least one of the plurality of sensors, that at least one of an inertial angle of a joint component of the artificial orthotic or prosthetic device, an inertial angle velocity of a joint component of the artificial orthotic or prosthetic device, a ground reaction force, torque on the knee joint, the angle of the knee joint, or a distance of a force vector from a joint component of the artificial orthotic or prosthetic device did not reach a second threshold value within a second fixed time after reducing the flexion resistance of the knee joint; and increasing the flexion resistance of the knee joint based upon at least one of the inertial angle of a joint component of the artificial orthotic or prosthetic device, the inertial angle velocity of a joint component of the artificial orthotic or prosthetic device, the ground reaction force, torque on the knee joint, the angle of the knee joint, or the distance of the force vector from a joint component of the artificial orthotic or prosthetic device not reaching the second threshold value within the second fixed time after reducing the flexion resistance of the knee joint.

14. The method of claim 1, further comprising:
determining that at least one of the plurality of sensors has failed; and
adjusting the flexion resistance and/or the extension resistance of the knee joint using information from the plurality of sensors that have not failed.

15. An artificial orthotic or prosthetic device comprising:
an upper leg part and a lower leg part coupled together at a knee joint;
a foot coupled to the lower leg part;
a plurality of sensors;
at least one actuator configured to adjust the flexion resistance of the knee joint; and
a control device;
wherein the control device is configured to determine, using information from at least one of the plurality of sensors, that an inertial angle of the lower leg part is decreasing relative to a vertical direction and an inertial angle velocity of the lower leg part is below a threshold value, wherein the inertial angle includes an angle between the lower leg part and a vertical line positioned behind the lower leg part and extending through an ankle portion of the prosthetic device; and
wherein the control device is configured to maintain or increase the flexion resistance of the knee joint in a standing phase based upon the inertial angle of the lower leg part decreasing relative to the vertical direction and the inertial angle velocity of the lower leg part is below the threshold value.

16. The method of claim 15, wherein the foot comprises a forefoot, the method further comprising:
determining, using information from at least one of the plurality of sensors, that the forefoot is loaded; and
wherein the step of maintaining or increasing the flexion resistance of the knee joint in the standing phase includes maintaining or increasing the flexion resistance of the knee joint in the standing phase based upon the forefoot being loaded.

17. The artificial orthotic or prosthetic device of claim 16, wherein the control device is configured to determine, using information from at least one of the plurality of sensors, that the loading on the forefoot is increasing; and
wherein the control device is configured to maintain or increase the flexion resistance of the knee joint in the standing phase based upon the increasing loading on the forefoot.

18. The artificial orthotic or prosthetic device of claim 15, further comprising a setting device configured to change a setting of the control device to (a) an activated setting where the control device is configured to maintain or increase the flexion resistance of the knee joint in a standing phase based upon the inertial angle of the lower leg part decreasing relative to the vertical direction and the inertial angle velocity of the lower leg part is below the threshold value or (b) a deactivated setting where the control device is not configured to maintain or increase the flexion resistance of the knee joint in a standing phase based upon the inertial angle of the lower leg part decreasing relative to the vertical direction and the inertial angle velocity of the lower leg part is below the threshold value.

* * * * *